United States Patent [19]

Goldstein et al.

[11] Patent Number: 5,401,761
[45] Date of Patent: Mar. 28, 1995

[54] THIAZOLIDINEDIONE HYPOGLYCEMIC AGENTS

[75] Inventors: Steven W. Goldstein, Mystic; Bernard Hulin, Essex, both of Conn.

[73] Assignee: Pfizer, Inc., New York, N.Y.

[21] Appl. No.: 162,075

[22] Filed: Dec. 9, 1993

[51] Int. Cl.$^6$ .................. C07D 417/14; A61K 31/425
[52] U.S. Cl. ..................................... 514/369; 548/183
[58] Field of Search ........................ 548/183; 514/369

[56] References Cited

U.S. PATENT DOCUMENTS

| | | | |
|---|---|---|---|
| 4,332,952 | 6/1982 | Schnur | 548/226 |
| 4,340,605 | 7/1982 | Kawamatsu et al. | 424/263 |
| 4,342,771 | 8/1982 | Schnur | 424/263 |
| 4,367,234 | 1/1983 | Schnur | 424/272 |
| 4,617,312 | 10/1986 | Schnur | 514/369 |
| 4,703,052 | 10/1987 | Eggler et al. | 514/337 |
| 4,725,610 | 2/1988 | Meguro et al. | 514/369 |

FOREIGN PATENT DOCUMENTS 283035A 9/1988 European Pat. Off. .
299620A 1/1989 European Pat. Off. .
428312A 11/1990 European Pat. Off. .

OTHER PUBLICATIONS

Shoda (Chem. Pharm. Bull, 30, 3580 (1982)).

*Primary Examiner*—Robert Gerstl
*Attorney, Agent, or Firm*—Peter C. Richardson; Gregg C. Benson; Mervin E. Brokke

[57] ABSTRACT

Compounds of the formula

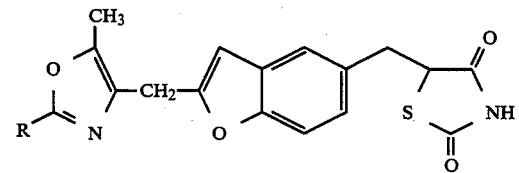

where R is alkyl, cycloalkyl, phenyl or substituted phenyl are useful as hypoglycemic agents.

14 Claims, No Drawings

THIAZOLIDINEDIONE HYPOGLYCEMIC AGENTS

BACKGROUND OF THE INVENTION

The present invention relates to certain compounds of the formula (I), depicted below, having utility as hypoglycemic and hypocholesteremic agents, methods for their use and pharmaceutical compositions containing them.

In spite of the early discovery of insulin and its subsequent wide-spread use in the treatment of diabetes, and the later discovery and use of sulfonylureas (e.g. chlorpropamide, tolbutamide, acetohexamide, tolazamide) and biguanides (e.g. phenformin) as oral hypoglycemic agents, the treatment of diabetes remains less than satisfactory. The use of insulin, necessary in about 10% of diabetic patients in which synthetic hypoglycemic agents are not effective (Type I diabetes, insulin dependent diabetes mellitus), requires multiple daily doses, usually by self injection. Determination of the proper dosage of insulin requires frequent estimations of the sugar in the urine or in the blood. The administration of an excess dose of insulin causes hypoglycemia, with effects ranging from mild abnormalities in blood glucose to coma, or even death. Treatment of non-insulin dependent diabetes mellitus (Type II diabetes) usually consists of a combination of diet, exercise, oral agents, e.g., sulfonylureas, and in more severe cases, insulin. However, the clinically available hypoglycemics are unfortunately fraught with other toxic manifestations which limit their use. In any event, where one of these agents may fail in an individual case, another may succeed. A continuing need for hypoglycemic agents, which may be less toxic or succeed where others fail, is clearly evident.

Furthermore, atherosclerosis, a disease of the arteries, is recognized to be the leading cause of death in the United States and Western Europe. The pathological sequence leading to atherosclerosis and occlusive heart disease has been described in detail by Ross and Glomset in New England Journal of Medicine 295, 369-377 (1976). The earliest stage in this sequence is the formation of "fatty streaks" in the carotid, coronary and cerebral arteries and in the aorta. These lesions are yellow in color due to the presence of lipid deposits found principally within smooth-muscle cells and in macrophages of the intima layer of the arteries and aorta. Cholesterol and cholesteryl ester account for most of this lipid. Further, it is postulated that most of the cholesterol found within the fatty streaks results from uptake from the plasma. These fatty streaks, in turn, give rise to development of the "fibrous plaque", which consists of accumulated intimal smooth muscle cells laden with lipid and surrounded by extra cellular lipid, collagen, elastin and proteoglycans. The cells plus matrix form a fibrous cap that covers a deeper deposit of cell debris and more extracellular lipid. The lipid is primarily free and esterified cholesterol. The fibrous plaque forms slowly, and is likely in time to become calcified and necrotic, advancing to the "complicated lesion" which accounts for the arterial occlusion and tendency toward mural thrombosis and arterial muscular spasm that characterize advanced atherosclerosis.

Epidemiological evidence has firmly established hypedipidemia as a primary risk factor in causing cardiovascular disease (CVD) due to atherosclerosis. In recent years, leaders of the medical profession have placed renewed emphasis on lowering plasma cholesterol levels, and low density lipoprotein cholesterol in particular, as an essential step in prevention of CVD. The upper limits of "normal" are now known to be significantly lower than heretofore appreciated. As a result, large segments of Western populations are now realized to be at high risk for development or progression of CVD because of this factor. Individuals who posses independent risk factors in addition to hypedipidemia are at particularly high risk. Such independent risk factors include glucose intolerance, left ventricular hypertrophy hypertension, and being of the male sex. Cardiovascular disease is especially prevalent among diabetic subjects, at least in part because of the existence of multiple independent risk factors. Successful treatment of hyperlipidemia in the general population, and in diabetic subjects in particular, is therefore of exceptional medical importance.

The first step in recommended therapeutic regimens for hyperlipidemia is dietary intervention. While diet alone produces adequate response in some individuals, many others remain at high risk and must be treated further by pharmacological means. New drugs for the treatment of hyperlipidemia are, therefore, of great potential benefit for large numbers of individuals at high risk of developing CVD. Further, successful treatment of both the hyperlipidemia and hyperglycemia associated with the diabetic state with a single therapeutic agent is particularly desirable.

In addition to the hypoglycemic agents cited above, a variety of other compounds have been reported to possess this type of activity, as reviewed by Blank [Burger's Medicinal Chemistry, Fourth Edition, Part II, John Wiley and Sons, N.Y. (1979), pp. 1057–1080].

Schnur, U.S. Pat. No. 4,367,234 discloses hypoglycemic oxazolidinediones of the formula

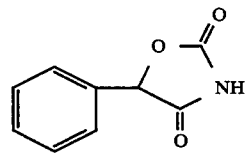

in which the phenyl ring is generally mono- or multi-substituted in the ortho/meta positions. Notably, with the exception of the 4-fluorophenyl analog, the para-substituted derivatives are either inactive or possess a low level of hypoglycemic activity. Schnur, U.S. Pat. Nos. 4,332,952 and 4,342,771 further disclose a variety of similar oxazolidinedione hypoglycemic agents which are alternatively substituted at the 5-position with a heterocyclic group. These include certain furan, thiophene, pyrrole and pyridine derivatives.

Schnur, U.S. Pat. No. 4,617,312 discloses hypoglycemic thiazolidinediones of the formula

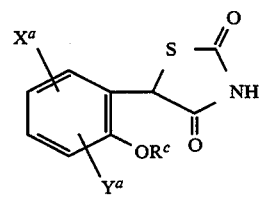

where $R^c$ is lower alkyl, $X^a$ is F, Cl or Br, and $Y^a$ is hydrogen, chloro, lower alkyl or lower alkoxy. Notably, the compounds require ortho-substitution with an alkoxy group, and para-substitution is limited to hydrogen or halogen. Shoda et al. (*Chem. Pharm. Bull.*, 30, 3563 (1982) describe the preparation of a series of 5-[4-(2-methyl-2-phenylpropoxy)benzyl]thiazolidine-2,4-diones as antidiabetic agents. Kawamatsu et al., U.S. Pat. No. 4,340,605, disclose hypoglycemic compounds of the formula

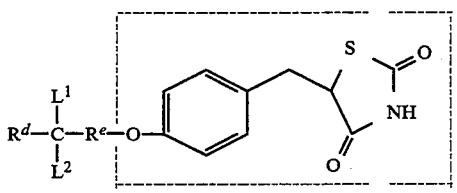

wherein $R^c$ is a bond or lower alkylene and when $R^d$ is an optionally substituted five- or six-membered heterocyclic group including one or two hetero-atoms selected from N, O and S; $L^1$ and $L^2$ may each be defined as hydrogen.

Eggler et al., U.S. Pat. No. 4,703,052, discloses hypoglycemic thiazolidinediones of the formula

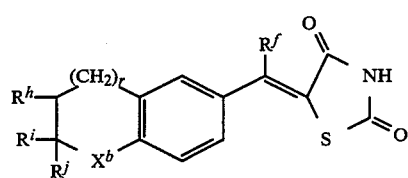

where the dotted line represents an optional bond, $R^f$ is H, methyl or ethyl, $X^b$ is O, S, SO, $SO_2$, $CH_2$, CO, CHOH or $NR^k$, $R^k$ is H or an acyl group and the numerous definitions of $R^g$, $R^h$, $R^i$ and $R^j$ as optionally substituted phenyl, benzyl, phenethyl or styryl.

Meguro et al., U.S. Pat. No. 4,725,610 disclose a sedes of hypoglycemic thiazolidinediones of the formula

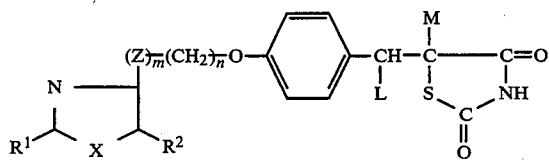

EP 283,035A and EP 299,620A describe benzoxazole and benzofuran linked thiazolidinediones as antidiabetic agents, EP 299,620A describes a compound of the formula:

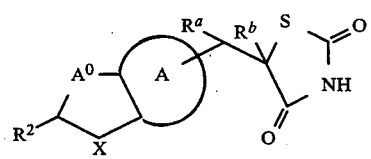

or a pharmaceutically acceptable salt thereof wherein $A^o$ represents nitrogen or a moiety $R^1$—C— wherein
$R^1$ represents hydrogen, alkyl or a substituted or unsubstituted aryl group;

$R^2$ represents a moiety $R^3$—Y—Z— wherein $R^3$ represents substituted or unsubstituted phenyl, substituted or unsubstituted pyridyl or a substituted or unsubstituted oxazolyl group, and Y represents —$(CH_2)_n$— wherein n represents zero or any integer in the range of 1 to 6 and Z represents —$CH_2$—, —CH(OH)— or —CO—;

$R^a$ and $R^b$ each represent hydrogen or $R^a$ and $R^b$ together represent a bond;

A represents a residue of a benzene ring, the carbon atoms of the residue having in total up to four substituents; and X represents O or S.

EP 299,620A encompasses the compounds of this invention in its broad generic disclosure; however, it does not describe or exemplify the compounds of the present invention, nor disclose how to make them. The compounds of the present invention show substantially greater hypoglycemic activity compared to the compounds of EP 299,620A.

SUMMARY OF THE INVENTION

The present invention relates to compounds of formula (I)

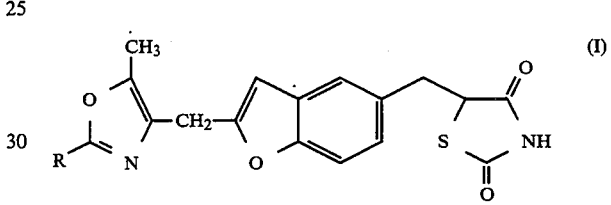

or a pharmaceutically acceptable salt thereof wherein R is alkyl of one to six carbon atoms, cycloalkyl of three to seven carbon atoms, phenyl or mono- or di-substituted phenyl wherein said substituents are independently alkyl of one to six carbon atoms, alkoxy of one to three carbon atoms, halogen or trifluoromethyl.

A preferred group of compounds is that of formula I wherein R is $(C_1$-$C_6)$alkyl, $(C_3$-$C_7)$cycloalkyl, phenyl, halophenyl or $(C_1$-$C_6)$alkylphenyl. Especially preferred within this group are the compounds where R is phenyl, methylphenyl, fluorophenyl, chlorophenyl or cyclohexyl.

The present invention also includes pharmaceutical compositions for use in hyperglycemic and hypercholesterolemic mammals which comprises blood sugar lowering and blood cholesterol lowering amounts, respectively, of a compound of formula I with a suitable carrier.

Also included are methods for lowering blood glucose or blood cholesterol in a hyperglycemic or hypercholesterolemic mammal, respectively, which comprises administering to said mammal a blood glucose lowering or blood cholesterol lowering amount of a compound of formula I.

DETAILED DESCRIPTION OF THE INVENTION

The expression "pharmaceutically-acceptable salts" is intended to define but is not limited to such base salts as the alkali metal salts, (e.g. sodium and potassium), alkaline earth metal salts (e.g. calcium and magnesium), aluminum salts, ammonium salts, and salts with organic amines such as benzathine (N,N'-dibenzylethylenediamine), choline, diethanolamine, ethylenediamine, meglumine (N-methylglucamine), benethamine (N-benzylphenethylamine) diethylamine, piperazine, trometha-
mine (2-amino-2-hydroxymethyl-1,3-propanediol) and
procaine.

The term "halogen or halo" includes fluoro, chloro, bromo and iodo. The term "alkyl" defines both straight and branched carbon chains including, but not limited to, methyl, ethyl, propyl, isopropyl, n-butyl, sec-butyl, iso-butyl, t-butyl and the like.

As used herein, the expression "reaction inert solvent" refers to those solvents which do not interact with starting materials, intermediates or products in a manner which adversely affects the yield of the desired product.

The compounds of formula I may be prepared by a variety of synthetic methods which will be obvious to the organic chemist of ordinary skill. One convenient synthetic route is illustrated below and described in Example 1 where R is phenyl.

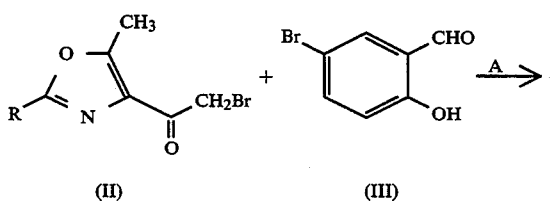

(II)     (III)

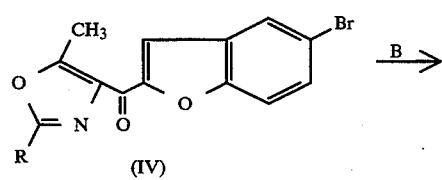

(IV)

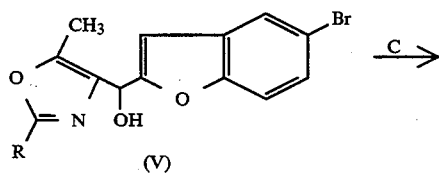

(V)

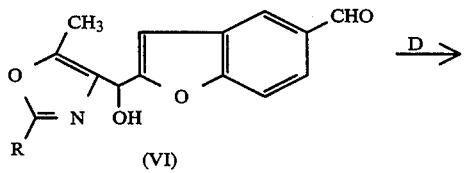

(VI)

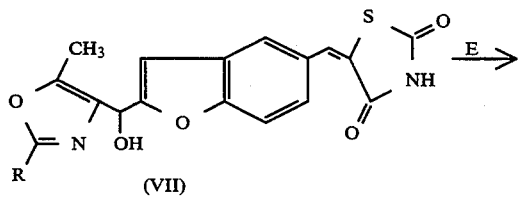

(VII)

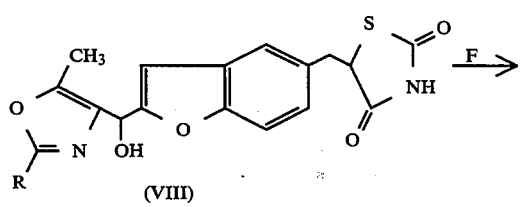

(VIII)

-continued

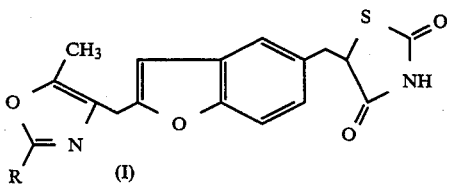

(I)

In reaction A, 5-bromosalicylaldehyde (III) is coupled with the appropriately substituted 4-haloacetyloxazole (II) in the presence of a base, preferably sodium methoxide or sodium ethoxide in a suitable solvent such as methanol, ethanol or propanol. The reactants are used in approximately equal quantities and it is preferred to first form the sodium salt of the 5-bromosalicylaldehyde in solution. The 4-haloacetyloxazole is then added and the resulting slurry is heated to 50°–100° C., preferably 78° C. for a period of 4 to 20 hours or until the reaction is complete. The product, an oxazol-4-ylcarbonyl-5-bromobenzofuran (IV), is collected by filtration after cooling the reaction mixture. The product may be purified by washing with solvent or other conventional means.

The product (IV) from reaction A may be used in reaction B in which the keto group is reduced to an alcohol group to form an oxazol-4-ylhydroxymethyl-5-bromobenzofuran (V).

The ketone product (IV) from reaction A is dissolved in a reaction inert solvent such as a mixture of an alcohol and an ether, for example, tetrahydrofuran and methanol, and cooled to about 0° C. A reducing agent, preferably sodium borohydride, is added over a period of 10–30 minutes, and the resulting mixture is stirred at approximately 0° C. for 30–60 minutes after which it is allowed to warm to room temperature and stirred for an additional 30–90 minutes. The solvent is then removed under reduced pressure and the product (V) is washed with water.

The alcohol product (V) from reaction B may be used in reaction C wherein it is converted to a 4-oxazolylhydroxymethyl-5-benzofurancarboxaldehyde (VI). The alcohol product (V) from reaction B is dissolved in a dry reaction inert solvent such as tetrahydrofuran, cooled to about −78° C. and treated slowly with a solution of n-butyllithium in hexanes and then with dimethylformamide in tetrahydrofuran. The mixture may then be warmed to room temperature and treated with an aqueous solution of ammonium chloride. The product may be isolated by extraction with a suitable solvent such as ethyl acetate followed by washing, drying and finally removal of the solvent. The resulting aldehyde (VI) may be purified by standard techniques such as recrystallization.

Reaction D involves the coupling of the 2-(4-oxazolylhydroxymethyl)-5-benzofurancarboxaldehyde (VI) from reaction C with 2,4-thiazolidinedione.

In step D, approximately equimolar amounts of the reactant (VI), wherein R is as defined above, and thiazolidinedione are heated in the presence of a mild base to provide the olefin of formula (VII). This step may be carded out in the presence of a reaction inert solvent or in the absence of solvent at a temperature which is sufficiently high to cause at least partial melting of the reaction mixture. A preferred such temperature is in the range of from 100° to 250° C., and especially preferred is a temperature of from 140° to 200° C.

Examples of suitable mild bases for the above reaction include the alkali metal and alkaline earth salts of weak acids such as the $(C_1-C_{12})$alkyl carboxylic acids and benzoic acid; alkali metal and alkaline earth carbonates and bicarbonates such as calcium carbonate, magnesium carbonate, potassium bicarbonate; and tertiary amines such as pyridine, N-methylmorpholine, N-ethylpiperidine and the like. An especially preferred mild base is sodium acetate for reasons of economy and efficiency.

In a typical such reaction the aldehyde or ketone starting material (VI) and thiazolidinedione are combined in approximately equimolar amounts with a molar excess, preferably a 2–4 fold molar excess, of anhydrous sodium acetate and the mixture is heated at a temperature high enough to effect melting, at which temperature the reaction is substantially complete in from about 5 to 60 minutes. The desired olefin of formula (VII) is then isolated, for example, by mixing with water and filtration, to obtain the crude product, which is purified, if desired, e.g. by crystallization or by standard chromatographic methods.

In a preferred method, this reaction takes place conveniently in a solvent such as ethanol in the presence of an organic base catalyst such as piperidine. The resulting solution is heated for 12–18 hours at the reflux temperature of the solvent, preferably about 80° C. An excess of 25–75% of thiazolidinedione is preferred to completely convert (VI) to the product. The solution is then cooled and the product isolated and purified to yield at 5-((2-(4-oxazolyl)hydroxymethyl)-5-benzofuranylmethylidene)-2,4-thiazolidinedione (VII).

Reaction E converts the methylidene product of reaction D (VII) to a 5-((2-(4-oxazolyl)hydroxymethyl)-5-benzofuranylmethyl)-2,4-thiazolidinedione (VIII) by reductive means.

The reduction of the olefins may be carried out by employing a wide variety of reducing agents which are known to reduce carbon-to-carbon double bonds, such as hydrogen in the presence of a noble metal catalyst. Typically, the hydrogenation is carried out in the presence of a reaction inert solvent.

When the reduction step is carried out employing hydrogen in the presence of a noble metal catalyst, a convenient method for carrying out this transformation is to stir or shake a solution of a compound of the formula (VII) under an atmosphere of hydrogen, or hydrogen mixed with an inert diluent such as nitrogen, in the presence of a noble metal hydrogenation catalyst. Suitable solvents for this reaction are those which substantially dissolve the starting compound of the formula (VII) but which do not themselves suffer hydrogenation or hydrogenolysis. Examples of such solvents include ethers such as diethyl ether, tetrahydrofuran, dioxane and 1,2-dimethoxyethane; low molecular weight esters such as ethyl acetate and butyl acetate; tertiary amides such as N,N-dimethylformamide, N,N-dimethylacetamide and N-methylpyrrolidone; and lower alkyl carboxylic acids such as formic, acetic, propionic and isobutyric acid. An especially preferred such solvent is glacial acetic acid.

Introduction of the hydrogen gas into the reaction medium is usually accomplished by carrying out the reaction in a sealed vessel, containing the compound of formula (VII), the solvent, the catalyst and the hydrogen. The pressure inside the reaction vessel can vary from about 1 to about 100 kg/cm$^2$. The preferred pressure range, when the atmosphere inside the reaction vessel is substantially pure hydrogen, is from about 2 to about 5 kg/cm$^2$. The hydrogenation is generally run at a temperature of from about 0° to about 60° C. and preferably from about 25° to about 50° C. Utilizing the preferred temperature and pressure values, hydrogenation generally takes place in a few hours, e.g., from about 2 hours to about 20 hours. The preferred noble metal catalysts used in this hydrogenation reaction are the type of agents known in the art for this kind of transformation; for example, nickel, palladium, platinum and rhodium. A palladium catalyst is preferred because such catalysts are not readily poisoned by sulfur. The catalyst is usually present in an amount from about 0.01 to about 25 weight-percent, based on the compound of formula (VII). It is often convenient to suspend the catalyst on an inert support; a particularly convenient catalyst is palladium suspended on an inert support such as carbon.

When the hydrogenation is substantially complete, the desired product of formula (VIII) is then isolated by standard methods, e.g., the catalyst is removed by filtration, the solvent evaporated and the product purified, if desired, by well known methods such as crystallization or by chromatography.

A preferred method for reduction of the compounds of formula (VII) to the corresponding compounds of formula (VIII) is by means of a metal-acid couple which produces hydrogen in situ.

Sodium amalgam is a preferred reducing agent. The reaction is conducted in a reaction inert solvent; for example, tetrahydrofuran. An alcohol such as methanol is added to the reaction to provide a source of hydrogen. The resulting slurry is stirred until the reaction is complete in about one hour at room temperature. The solvent is decanted and the residue is washed with solvent, treated with dilute aqueous acid and extracted with solvent. The combined organic extracts are washed, dried and concentrated to yield the product which may be purified by conventional means such as flash chromatography if desired.

Reaction F converts the product of reaction E (VIII) to the compound of formula I by removing the hydroxyl group with triethylsilane in about 2–3 molar excess in a strong organic acid such as trifluoroacetic acid. The above mixture is heated, preferably at reflux until the reaction is completed, usually in 1–2 hours; it is then diluted with a solvent such as ethyl acetate which is washed with water and dilute bicarbonate. The product is isolated by removing the solvent. If desired, the product may be purified by crystallization from a suitable solvent such as ethanol.

Sodium amalgam is a preferred reducing agent. The reaction is conducted in a reaction inert solvent; for example, tetrahydrofuran. An alcohol such as methanol is added to the reaction to provide a source of hydrogen. The resulting slurry is stirred until the reaction is complete in about one hour at room temperature. The solvent is decanted and the residue is washed with solvent, treated with dilute aqueous acid and extracted with solvent. The combined organic extracts are washed, dried and concentrated to yield the product which may be purified by conventional means such as flash chromatography if desired.

Reaction F converts the product of reaction E (VIII) to the compound of formula I by removing the hydroxyl group with triethylsilane in about 2–3 molar excess in a strong organic acid such as trifluoroacetic acid. The above mixture is heated, preferably at reflux until the reaction is completed, usually in 1–2 hours; it is then diluted with a solvent such as ethyl acetate which is washed with water and dilute bicarbonate. The product is isolated by removing the solvent. If desired, the product may be purified by crystallization from a suitable solvent such as ethanol.

Another procedure for removal of the hydroxyl group is hydrogenation of the alcohol (VIII) over Pd at high pressure or high temperature.

The oxazole compounds (II) used in this invention may be prepared by methods described in the chemical literature and which are generally known to the chemist of ordinary skill. Typical procedures for preparation of the starting oxazole compounds (II) may be found in U.S. Pat. No. 4,725,610 and references cited therein which are incorporated herein by reference.

Other reagents used to prepare the compounds of this invention are readily available from commercial sources or the processes to prepare the reagents are described herein or in the chemical literature and would be known to those of ordinary skill in the art.

The pharmaceutically-acceptable cationic salts of the compounds of the present invention are readily prepared by reacting the acid forms with an appropriate base, usually one equivalent, in a co-solvent. Typical bases are sodium hydroxide, sodium methoxide, sodium ethoxide, sodium hydride, potassium methoxide, magnesium hydroxide, calcium hydroxide, benzathine, choline, diethanolamine, piperazine and tromethamine. The salt is isolated by concentration to dryness or by addition of a non-solvent. In many cases, salts are preferably prepared by mixing a solution of the acid with a solution of a different salt of the cation (sodium or potassium ethylhexanoate, magnesium oleate), employing a solvent (e.g., ethyl acetate) from which the desired cationic salt precipitates, or can be otherwise isolated by concentration and/or addition of a non-solvent.

The reactions employed to prepare the compounds of this invention can generally be monitored by standard thin layer chromatographic (tlc) methods, employing commercially available plates. Suitable eluants are common solvents such as chloroform, ethyl acetate or hexane or suitable combinations thereof which will differentiate starting materials, products, by-products, and in some cases intermediates. Applying these methods, which are well known in the art, will permit further improvement in the methodology of the specific examples detailed hereinafter, e.g., the selection of more optimal reaction times and temperatures, as well as aid in the selection of optimal processes.

The present compounds of the formula (I) are readily adapted to clinical use as hypoglycemic or hypocholesterolemic agents. The activity required for the former clinical use is defined by the test for hypoglycemic effect in ob/ob mice by the following procedure:

Five to eight week old C57 BL/6J-ob/ob mice (obtained from Jackson Laboratory, Bar Harbor, Me.) were housed five per cage under standard animal care practices. After a one week acclimation period, the animals were weighed and 25 microliters of blood was collected via an ocular bleed prior to any treatment. The blood sample was immediately diluted 1:5 with saline containing 2.5 mg/ml sodium fluoride and 2% sodium heparin, and held on ice for metabolite analysis. Animals were then dosed daily for five days with drug (5–50 mg/kg), a positive control (50 mg/kg) of ciglitazone; U.S. Pat. No. 4,467,902; Sohda et al., Chem. Pharm. Bull., vol. 32, pp. 4460–4465, 1984), or vehicle.

All drugs were administered in a vehicle consisting of 0.25% w/v methyl cellulose. On day 5, the animals were weighed again and bled (via the ocular route) for blood metabolite levels. The freshly collected samples were centrifuged for two minutes at 100,000× g at room temperature. The supernatant was analyzed for glucose, for example, by the ABA 200 Bichromatic Analyzer TM [*], using the A-gent TM [1] glucose UV reagent system[*2] (hexokinase method) using 20, 60 and 100 mg/dl standards. Plasma glucose was then calculated by the equation, $$\text{Plasma glucose (mg/dl)} = \text{Sample value} \times 5 \times 1.67 = 8.35 \times \text{Sample value}$$

where 5 is the dilution factor and 1.67 is the plasma hematocrit adjustment (assuming the hematocrit is 40%).

[1] A registered trademark of Abbot Laboratories, Diagnostics Division, 820 Mission Street, So. Pasadena, Calif. 91030.
[2*] A modification of the method of Richterich and Dauwalder, Schweizerische Medizinische Wochenschrift, 101, 860 (1971).

The animals dosed with vehicle maintain substantially unchanged hyperglycemic glucose levels (e.g., 250 mg/dl), while positive control animals have depressed glucose levels (e.g., 130 mg/dl). Test compounds are reported in terms of % glucose normalization. For example, a glucose level which is the same as the positive control is reported as 100%.

Studies such as that described below demonstrate that the compounds of formula (I) effect the lowering of serum cholesterol levels in mammals.

Female mice (strain C57Br/cd J), obtained from Jackson Laboratories, Bar Harbor, Me., are used at 8–12 weeks, following 2–4 weeks acclimation having free access to water and standard laboratory chow. Animals are dived randomly into three groups of 6–7 animals. All three groups are placed on a diet containing 0.75% cholesterol, 31% sucrose, 15.5% starch, 20% casein, 17% cellulose, 4.5% corn oil, 5% coconut oil, 0.25% cholic acid, 4% salts and 2% vitamin; permitted to feed ad lib for 18 days; and dosed daily at 9–11 a.m. for the final 5 days by oral gavage, the control group with 5 ml/kg of vehicle (0.1% aqueous methyl cellulose) and the test groups with the compound under study at a dose range of 0.1–20 mg/kg/day in vehicle. After the fourth day of dosing, the animals are fasted overnight, starting at 5 p.m. The following morning a fifth and final dose of the compound is administered to the test groups and, three hours later, the animals are sacrificed by decapitation. Blood from the body trunk is collected and allowed to clot, and the serum assayed enzymatically, using an Abbot VP automated analyzer, for HDL cholesterol, LDL and VLDL cholesterol, and total cholesterol. Whether judged on the basis LDL+VLDL cholesterol levels, total cholesterol levels or the ratio of LDL+VLDL/HDL, the compounds of this invention generally show favorable result in lowering cholesterol levels.

The present compounds of the formula (I) are clinically administered to mammals, including man, via either the oral or the parenteral route. Administration by the oral route is preferred, being more convenient and avoiding the possible pain and irritation of injection. However, in circumstances where the patient cannot swallow the medication, or absorption following oral administration is impaired, as by disease or other abnormality, it is essential that the drug be administered parenterally. By either route, the dosage is in the range of about 0.10 to about 50 mg/kg body weight of the subject per day, preferably about 0.10 to about 10 mg/kg body weight per day administered singly or as a divided dose. However, the optimum dosage for the individual subject being treated will be determined by the person responsible for treatment, generally smaller doses being administered initially and thereafter increments made to determine the most suitable dosage. This will vary according to the particular compound employed and with the subject being treated.

The compounds can be used in pharmaceutical preparations containing the compound, or pharmaceutically acceptable acid salt thereof, in combination with a pharmaceutically-acceptable carrier or diluent. Suitable pharmaceutically-acceptable carriers include inert solid fillers or diluents and sterile aqueous or organic solutions. The active compound will be present in such pharmaceutical compositions in amounts sufficient to provide the desired dosage amount in the range described above. Thus, for oral administration the compounds can be combined with a suitable solid or liquid carrier or diluent to form capsules, tablets, powders, syrups, solutions, suspensions and the like. The pharmaceutical compositions may, if desired, contain additional components such as flavorants, sweeteners, excipients and the like. For parentered administration the compounds can be combined with sterile aqueous or organic media to form injectable solutions or suspensions. For example, solutions in sesame or peanut oil, aqueous propylene glycol and the like can be used, as well as aqueous solutions of water-soluble pharmaceutically-acceptable salts of the compounds. The injectable solutions prepared in this manner can then be administered intravenously, intraperitoneally, subcutaneously, or intramuscularly, with intramuscular administration being the preferred parenteral route in man.

The present invention is illustrated by the following Examples. However, it should be understood that the invention is not limited to the specific details of these examples.

EXAMPLE 1

5-[(2-(5-Methyl-2-phenyl-4-oxazolyl)methyl-5-benzofuranylmethyl]-2,4-thiazolidinedione

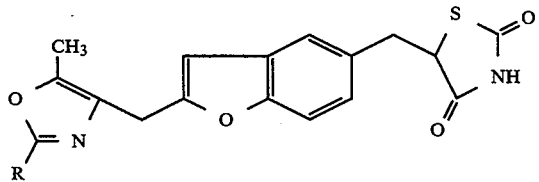

A. 2-(2-Phenyl-5-methyloxazol-4-ylcarbonyl)-5-bromobenzofuran

To a slurry of 294 g of 5-bromosalicylaldehyde in 3 liters of dry ethanol was added 79.06 g of sodium mathoxide and the mixture allowed to stir for 20 minutes. To the resulting yellow slurry was added 410 g of 2-phenyl-4-bromoacetyl-5-methyloxazole and the slurry heated to 78° C. for 2 hours. An additional 2.5 g of sodium methoxide was added and heating continued overnight under a nitrogen atmosphere. The reaction was cooled and the solids filtered and washed with ethanol, 393 g, m.p. 212°-213° C.

B. 2-(2-Phenyl-5-methyloxazol-4-ylhydroxymethyl)-5-bromobenzofuran

To a slurry of 265.44 g of the product of Example 1-A in 2.1 liters of tetrahydrofuran was added 2.5 liters of absolute methanol and the slurry cooled in an ice bath. Sodium borohydride (26.3 g) was added in four portions over a period of 15 minutes. After stirring in the cold for 30 minutes, the reaction mixture was allowed to warm to room temperature. After 1 hour the solvent was removed in vacuo and the residue treated with 3 liters of water. The solids were filtered, washed with water and dried in vacuo, 221.48 g, m.p. 152°-154° C.

C. 2-[(5-Methyl-2-phenyl-4-oxazolyl)hydroxymethyl]-5-benzofurancarboxaldehyde

To a solution of the product of 1B (10 g, 26 mmol) in dry tetrahydrofuran (425 ml) was added at −78° C. a 1.6M solution of n-butyllithium in hexanes (65 ml, 0.10 mol) over 30 minutes. The red-purple solution was stirred for 30 minutes at −78° C., then a solution of dimethylformamide (10 ml, 0.13 mol) in tetrahydrofuran (25 ml) was added. The mixture was warmed to room temperature, diluted with saturated aqueous ammonium chloride (500 ml) and extracted with ethyl acetate (2×200 ml). The combined extracts were washed with water (150 ml) and brine (200 ml), dried over sodium sulfate and concentrated. The residue was recrystallized from ethyl acetate (240 ml) to give an off-white solid (4.2 g).

D. 5-[(2-(5-Methyl-2-phenyl-4-oxazolyl)hydroxymethyl)-5-benzofuranylmethylidene]-2,4-thiazolidinedione A solution of 2-[(5-methyl-2-phenyl-4-oxazolyl)-hydroxymethyl]-5-benzofurancarboxaldehyde (1.0 g, 3.0 mmol), 2,4-thiazolidinedione (0.53 g, 4.5 mmol) and piperidine (5 drops) in ethanol (25 ml) was heated to reflux overnight. The solution was cooled and the precipitated solid was filtered (0.75 g).

E. 5-[(2-(5-Methyl-2-phenyl-4-oxazolyl)hydroxymethyl)-5-benzofuranylmethyl]-2,4-thiazolidinedione To a slurry of 5-[(2-(5-methyl-2-phenyl-4-oxazolyl)-hydroxymethyl)-5-benzofuranylmethylidene]-2,4-thiazolidinedione (0.75 g, 1.7 mmol) in methanol (15 ml) and tetrahydrofuran (15 ml) was added 3% sodium amalgam (5 g). The mixture was stirred for 1 hour, then decanted. The residue was rinsed with methanol and the combined solutions were concentrated. The residue was slurried in 0.1N hydrochloric acid (60 ml) and extracted with chloroform (2×70 ml). The combined extracts were washed with water (30 ml) and brine (30 ml), dried over sodium sulfate and concentrated. The product was purified by flash-chromatography (hexanes/ethyl acetate, 1:1) and obtained as a white solid (0.46 g).

F. 5-[(2-(5-Methyl-2-phenyl-4-oxazolyl)methyl)-5-benzofuranylmethyl]-2,4-thiazolidinedione To a solution of 5-[(2-(5-methyl-2-phenyl-4-oxazolyl)hydroxymethyl)-5-benzofuranylmethyl]-2,4-thiazolidinedione (0.23 g, 0.53 mmol) in trifluoroacetic acid (3 ml) was added triethylsilane (0.21 ml, 1.3 mmol). The solution was heated to reflux for 1 hour, then diluted with ethyl acetate (50 ml), washed with water (2×30 ml), saturated sodium bicarbonate (carefully) (2×30 ml), water (30 ml) and brine (30 ml), dried over sodium sulfate and concentrated. The tacky solid was recrystallized from ethanol (8–10 ml) and water (a few drops) to give white crystals (110 mg, m.p. 160°-161° C.).

EXAMPLES 2–9

Examples 2–9 were prepared following the general procedure of Example 1 using the appropriately 2-substituted 4-bromoacetyl-5-methyloxazole as starting material.

Example 2

5-[(2-(2-(4-chlorophenyl)-5-methyl-4-oxazolyl)methyl)-5-benzofuranylmethyl]-2,4thiazolidinedione; (m.p. 121°-123° C.)

Example 3

5-[(2-(5-methyl-2-(1,1-dimethylethyl)-4-oxazolyl)-methyl)-5-benzofuranylmethyl]-2,4-thiazolidinedione; (m.p. 205°-208° C.)

Example 4

5-[(2-(5-methyl-2-(4-methylphenyl)-4-oxazolyl)-methyl)-5-benzofuranylmethyl]-2,4-thiazolidinedione; (m.p. 184°-186° C.)

Example 5

5-[(2-(2-(3-fluorophenyl)-5-methyl-4-oxazolyl)methyl)-5-benzofuranylmethyl]-2,4-thiazolidinedione; (m.p. 165°-167° C.)

Example 6

5-[2-(5-methyl-2-(2-methylphenyl)-4-oxazolyl)-methyl)-5-benzofuranylmethyl]-2,4-thiazolidinedione; (m.p. 137.5°-140.5° C.)

Example 7

5-[(2-(5-methyl-2-(3-methylphenyl)-4-oxazolyl)-methyl)-5-benzofuranylmethyl]2,4-thiazolidinedione; (m.p. 189.5°-191° C.)

Example 8

5- [(2-(2-cyclohexyl-5-methyl-4-oxazolyl)methyl)-5-benzofuranylmethyl]-2,4-thiazolidinedione; (m.p. 166°-170° C.)

Example 9

5-[(2-(2-(2-fluorophenyl)-5-methyl-4-oxazolyl)methyl)-5-benzofuranylmethyl]-2,4-thiazolidinedione; (m.p. 160.5°-162° C.)

EXAMPLE 10

Compounds of this invention were compared with the structurally related alcohols of EP 299620A with respect to hypoglycemic activity in the mouse by the procedure described above. The results were as follows:

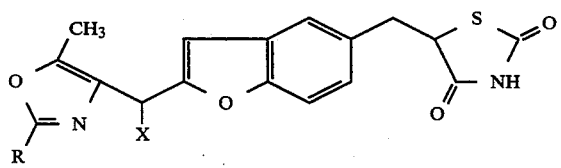

| | HYPOGLYCEMIC ACTIVITY IN THE OB/OB MOUSE | |
|---|---|---|
| | Present Invention X = H | EP 299620A X = OH |
| R | ED$_{50}$* (mg/kg) | ED$_{50}$* (mg/kg) |
| phenyl | 0.01 | 0.25 |
| p-chlorophenyl | 0.05 | |

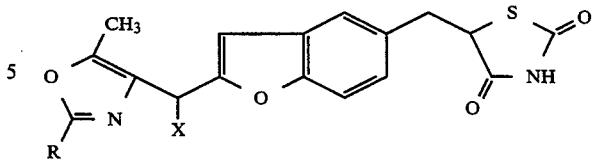

| | HYPOGLYCEMIC ACTIVITY IN THE OB/OB MOUSE | |
|---|---|---|
| | Present Invention X = H | EP 299620A X = OH |
| R | ED$_{50}$* (mg/kg) | ED$_{50}$* (mg/kg) |
| tert-butyl | 0.10 | |
| p-methylphenyl | 0.05 | |
| m-fluorophenyl | 0.05 | 0.50 |
| o-methylphenyl | 0.05 | >1 |
| m-methylphenyl | <0.005 | 0.05-0.1 |
| cyclohexyl | 0.05 | |
| o-fluorophenyl | 0.01 | 0.50 |

*Concentration required to give hypoglycemic activity equivalent to 50% of the positive control.

We claim:

1. A compound of the formula

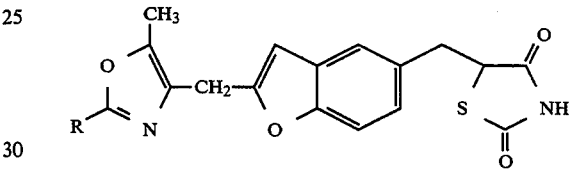

or a pharmaceutically acceptable salt thereof wherein R is alkyl having from one to six carbon atoms, cycloalkyl having three to seven carbon atoms, phenyl or mono- or di-substituted phenyl wherein said substituents are independently alkyl having one to six carbon atoms, alkoxy having one to three carbon atoms, halogen or trifluoromethyl.

2. A compound of claim 1 wherein R is (C$_1$-C$_6$)alkyl, (C$_3$-C$_7$)cycloalkyl, phenyl, halophenyl or (C$_1$-C$_6$)alkylphenyl.

3. A compound of claim 1 wherein R is phenyl, chlorophenyl, fluorophenyl, methylphenyl or cyclohexyl.

4. The compound of claim 1, wherein R is phenyl.

5. The compound of claim 1, wherein R is p-chlorophenyl.

6. The compound of claim 1, wherein R is tert-butyl.

7. The compound of claim 1 wherein R is p-methylphenyl.

8. The compound of claim 1 wherein R is o-methylphenyl.

9. The compound of claim 1 wherein R is m-methylphenyl.

10. The compound of claim 1 wherein R is o-fluorophenyl.

11. The compound of claim 1 wherein R is cyclohexyl.

12. The compound of claim 1 wherein R is m-fluorophenyl.

13. A pharmaceutical composition for use in a hyperglycemic mammal which comprises a blood glucose lowering amount of a compound of claim 1 and a pharmaceutically acceptable carrier.

14. A method of lowering the blood glucose in a hyperglycemic mammal which comprises administering to said mammal a blood glucose lowering effective amount of a compound of claim 1.

* * * * *